(12) United States Patent
Wada

(10) Patent No.: US 8,274,654 B2
(45) Date of Patent: Sep. 25, 2012

(54) APPARATUS FOR MEASURING NANOPARTICLES

(75) Inventor: Yukihisa Wada, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 470 days.

(21) Appl. No.: 12/663,772

(22) PCT Filed: Jun. 13, 2007

(86) PCT No.: PCT/JP2007/061919
§ 371 (c)(1),
(2), (4) Date: Dec. 9, 2009

(87) PCT Pub. No.: WO2008/152712
PCT Pub. Date: Dec. 18, 2008

(65) Prior Publication Data
US 2010/0177311 A1    Jul. 15, 2010

(51) Int. Cl.
*G01N 15/02* (2006.01)
*G01N 21/00* (2006.01)
(52) U.S. Cl. .................. 356/336; 356/335; 356/337
(58) Field of Classification Search ........... 356/335–344
See application file for complete search history.

(56) References Cited

U.S. PATENT DOCUMENTS

| | | | | |
|---|---|---|---|---|
| 5,038,043 A | * | 8/1991 | Dorion et al. | 250/374 |
| 5,459,406 A | * | 10/1995 | Louge | 324/688 |
| 6,040,573 A | * | 3/2000 | Sporleder et al. | 250/281 |
| 6,764,583 B2 | * | 7/2004 | Miles | 204/452 |
| 8,007,332 B2 | * | 8/2011 | Joshi et al. | 445/23 |

* cited by examiner

*Primary Examiner* — Gregory J Toatley
*Assistant Examiner* — Jarreas C Underwood
(74) *Attorney, Agent, or Firm* — Cheng Law Group, PLLC

(57) ABSTRACT

A dielectric sheet 3 is arranged between a pair of electrodes 2a and 2b for forming an electric field in a cell 1 that stores therein a sample having particles dispersed movably in a medium, the dielectric sheet 3 being formed to include multiple mutually parallel slits 3a to form a diffraction grating, and a parallel light flux is applied to the diffraction grating to generate diffracted light. A gradient electric field in the vicinity of the slits 3a generated by applying a voltage between the electrodes 2a and 2b causes the particles P to migrate in such a manner as to cover the slits 3a or away from the slits 3a and thereby the contrast of the diffraction grating to vary, and whereby the diffusion coefficient and/or size of the particles P can be calculated from the temporal change of the diffracted light when the particles diffuse freely after stopping the application of the voltage. In this measurement apparatus, the particles P might not migrate toward the electrodes 2a and 2b and are not absorbed there, which can prevent damage of the electrodes 2a and 2b and also the occurrence of an electrode reaction.

12 Claims, 5 Drawing Sheets

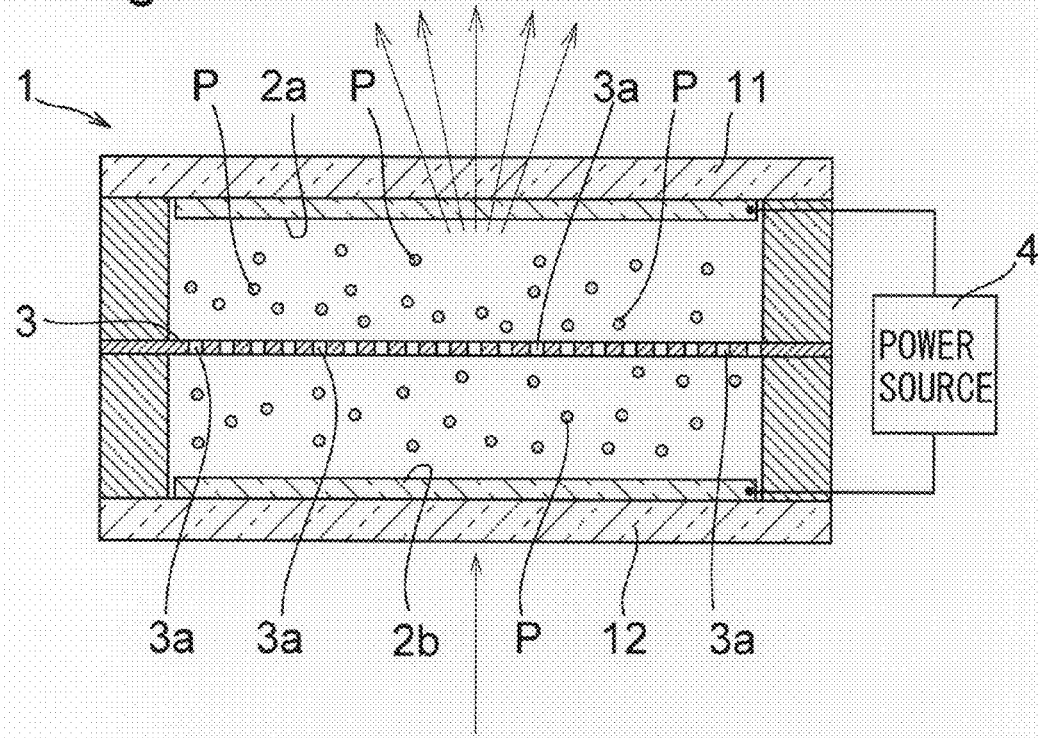
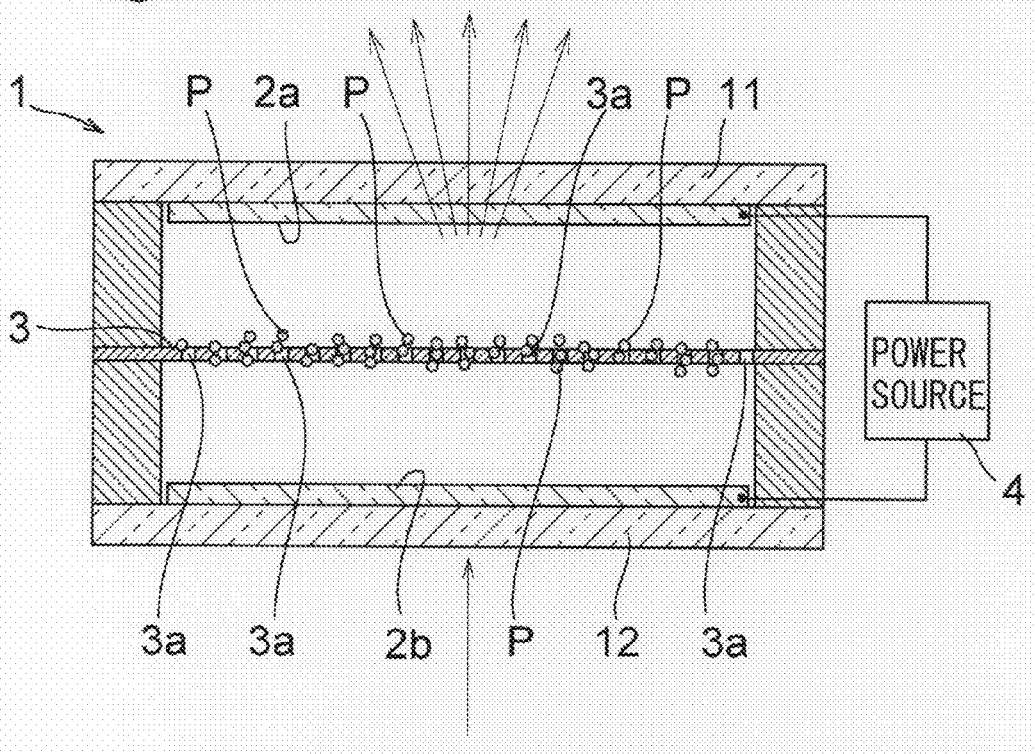

APPARATUS FOR MEASURING NANOPARTICLES

TECHNICAL FIELD

The present invention relates to an apparatus for optically measuring the diffusion coefficient and particle size of so-called nanoparticles with a diameter of 100 nm or less.

BACKGROUND ART

Particles with a diameter of 100 nm or less are generally called nanoparticles, and are just beginning to be used in various fields because they have properties different from those of general bulk materials of even the same material. Various methods for measuring particle size have been known including the laser diffraction/scattering method. Among them, methods based on the so-called dynamic scattering method (photon correlation method) have been employed mainly for nanoparticles with a diameter of 100 nm or less (refer to Patent Literatures 1 and 2 for example).

The dynamic scattering method utilizes the Brownian motion of particles, including exposing particles performing a Brownian motion in a medium to a light beam, measuring the intensity of scattered light from the particles at a predetermined position, and capturing the fluctuation of the scattered light intensity caused by the Brownian motion of the particles, that is, the temporal change of the scattered light. That is, the method utilizes the fact that to-be-measured particles each perform a Brownian motion with intensity according to its particle size to thereby calculate the particle size distribution of the particles.

However, in the dynamic scattering method (photon correlation method), in which the fluctuation of scattered light from particles is measured, it is necessary to measure a small fluctuation in intense scattered light, that is, to measure the fluctuation of light intensity in a bright field of view. Due to its principle, the problems of poor measurement sensitivity as well as poor S/N cannot be avoided.

As a powerful approach for solving such unavoidable problems in the dynamic scattering method, there has been proposed a method and apparatus for electrophoresing particles dispersed movably in a medium by applying a spatially periodic electric field to the particles, generating a quasi diffraction grating by making the particles have a spatially periodic alteration in concentration, in this state detecting diffracted light obtained by exposing the particles to a laser beam, and thereby calculating the diffusion coefficient and size of the particles from the temporal change of the diffracted light after stopping the application of the electric field (refer to Patent Literature 3).

This proposed method and apparatus utilizes dielectrophoresis or electrophoresis of particles in a medium, including generating a diffraction grating resulting from the concentration distribution (density distribution) of the particles by applying an electric field and, in this state, annihilating the diffraction grating by stopping the application of the electric field, that is, utilizes the fact that the annihilation process depends on the diffusion coefficient of the particles. The diffusion coefficient and therefore the size of the particles can be calculated from the time required for dissipation of diffracted light from the diffraction grating generated from the concentration distribution of the particles.

The apparatus has a specific configuration to apply a spatially periodic electric field to particles dispersed movably in a medium, in which a sample having particles dispersed movably in a medium is housed in a transparent cell, a comb-like electrode pair is formed on the inner surface of portions of wall bodies forming the cell, an AC or DC voltage is made applicable to the electrode pair, a parallel light flux such as a laser beam is applied externally to the portion where the electrode pair is formed in the cell 1, and a detection optical system is provided and adapted to detect diffracted light from a diffraction grating formed through the density distribution of the particles in a specified direction.

In accordance with this proposed method and apparatus, the intensity of diffracted light from the diffraction grating resulting from the concentration distribution of particles is detected, and thus the intensity is greater than that of scattered light from particles obtained in the dynamic scattering method, thereby a more intense signal is to be measured, resulting in a significant improvement in S/N and sensitivity relative to the dynamic scattering method.

Patent Literature 1: U.S. Pat. No. 5,094,532
Patent Literature 2: Japanese Patent Laid-Open Publication No. 2001-159595
Patent Literature 3: Japanese Patent Laid-Open Publication No. 2006-84207

DISCLOSURE OF THE INVENTION

Problems to be Solved by the Invention

Meanwhile, the apparatus configuration for implementing the proposed method above, which employs as mentioned above the arrangement that the electrodes are formed on the inner surface of the cell to form a spatially periodic electric field within the sample in the cell, suffers from a problem in that applying an AC voltage to the electrodes to form an AC electric field in the cell causes nanoparticles to migrate dielectrophoretically toward the electrodes and the migration speed to be maximized in the vicinity of the electrodes, which may cause nanoparticles to be absorbed onto the electrodes and the inner wall surface of the cell where the electrode pair is formed and thereby weaken the dielectrophoresis.

In addition, as particles are made concentrated with the voltage being kept applied to the electrodes, an electrode reaction may occur and, in this case, the electrode pair may deteriorate.

The present invention is an improvement to the above-described proposed technique of measuring the diffusion coefficient and/or size of particles from the temporal change of diffracted light from a diffraction grating resulting from the density distribution of the particles, and an object thereof is to provide an apparatus for measuring nanoparticles in which absorption of particles onto electrodes and/or surfaces where the electrodes are formed can be prevented and the occurrence of an electrode reaction can also be prevented effectively.

Means for Solving the Problems

In order to achieve the foregoing object, the present invention is directed to an apparatus for measuring nanoparticles including: a cell for storing therein a sample having particles dispersed movably in a medium; a power source for generating an AC or DC voltage; a pair of electrodes formed inside the cell in such a manner as to approximately face each other and to which a voltage is applied from the power source; a dielectric sheet arranged between the pair of electrodes and adapted to form a spatially periodic electric field in the cell with the application of the voltage between the electrodes; an irradiation optical system for applying a parallel light flux into the cell; a detection optical system for detecting diffracted light generated by the parallel light flux transmitting through the cell; control means for controlling the application of the voltage from the power source to the pair of electrodes; and data processing means for calculating the diffusion coefficient and/or size of the particles in the cell from the temporal change of the diffracted light through the application of the voltage and the stopping or modulation of the application.

The present invention may be arranged in such a manner that the cell includes wall bodies made of transparent material and facing each other, the pair of electrodes are transparent ones and formed on the mutually facing wall bodies, the dielectric sheet is provided between and in parallel with the wall bodies, the irradiation optical system is adapted to apply a parallel light flux into the cell through one of the transparent electrodes, and the detection optical system is adapted to detect diffracted light through the other transparent electrode.

The present invention may also be arranged in such a manner that the cell likewise includes wall bodies made of transparent material and facing each other, the pair of electrodes, which are not restricted to transparent ones, are each formed at an end portion of each wall body, the dielectric sheet is provided between and in parallel with the wall bodies, the irradiation optical system is adapted to apply a parallel light flux into the cell not through either of the pair of electrodes but through one of the wall bodies, and the detection optical system is adapted to detect diffracted light not through either of the pair of electrodes but through the other wall body.

The dielectric sheet of the present invention may be formed to include multiple mutually parallel slits, may be formed to include multiple mutually parallel hole arrays, each of the hole arrays including multiple through holes formed in a one-dimensional direction, or may be formed to include multiple through holes, each of the through holes being formed in a positional relationship of forming arrays in multiple directions.

The present invention utilizes the principle that providing a dielectric sheet between a pair of electrodes causes a gradient electric field to occur in the vicinity of the dielectric sheet when a voltage is applied between the pair of electrodes.

That is, when a dielectric sheet with multiple mutually parallel slits or multiple mutually parallel arrays of through holes formed therein is arranged between a pair of electrodes approximately facing each other n a cell and a voltage is applied between the pair of electrodes to form an electric field therebetween, the electric lines of force are concentrated at the positions where the slits or through holes are formed in the dielectric sheet to pass through the slits or through holes. That is, a spatially periodic electric field is formed in the cell.

When such a spatially periodic electric field is formed in the cell with a sample having particles dispersed movably in a medium being stored in the cell, the particles are drawn dielectrophoretically (when the applied voltage is AC) or electrophoretically (when the applied voltage is DC) to move toward high-density areas of the electric field (positive migrating force) or move repulsively away from the high-density areas (negative migrating force).

The multiple slits or multiple arrays of through holes in the dielectric sheet form a diffraction grating, and the contrast of the diffraction grating formed by the slits or arrays of through holes in the dielectric sheet varies due to the movement of the particles. That is, the particles, when moving under the positive migrating force, depart from the original homogeneously-dispersed state to be trapped in such a manner as to cover the slits or arrays of through holes in the dielectric sheet, resulting in a reduction in the contrast of the diffraction grating. On the contrary, the particles, when moving under the negative migrating force, depart from the original homogeneously-dispersed state to move away from the slits or arrays of through holes in the dielectric sheet, resulting in an increase in the contrast of the diffraction grating.

The parallel light flux applied into the cell transmits through the multiple slits or multiple arrays of through holes to be diffracted and the diffracted light is detected by the detection optical system. When the contrast of the diffraction grating varies due to the migration of the particles through the application of the electric field, the diffracted light intensity detected by the detection optical system also varies. In the state where the contrast of the diffraction grating varies due to the migration of the particles through the application of the electric field, when the application of the electric field is stopped or modulated, the particles start to diffuse freely to recover their original dispersion state in due course. The speed of the recovery depends on the diffusion coefficient of the particles. Accordingly, it is possible to calculate the diffusion coefficient and therefore the size of the particles from the temporal change in the intensity of diffracted light after migrating the particles through the application of the electric field and then stopping or modulating the application to trigger the diffusion.

BRIEF DESCRIPTION OF THE DRAWINGS

FIG. 2 is a schematic cross-sectional view of a cell in FIG. 1, where (A) shows a state where particles are dispersed and (B) shows a state where particles are trapped in the vicinity of slits;

REFERENCE NUMERALS

Figure 1:
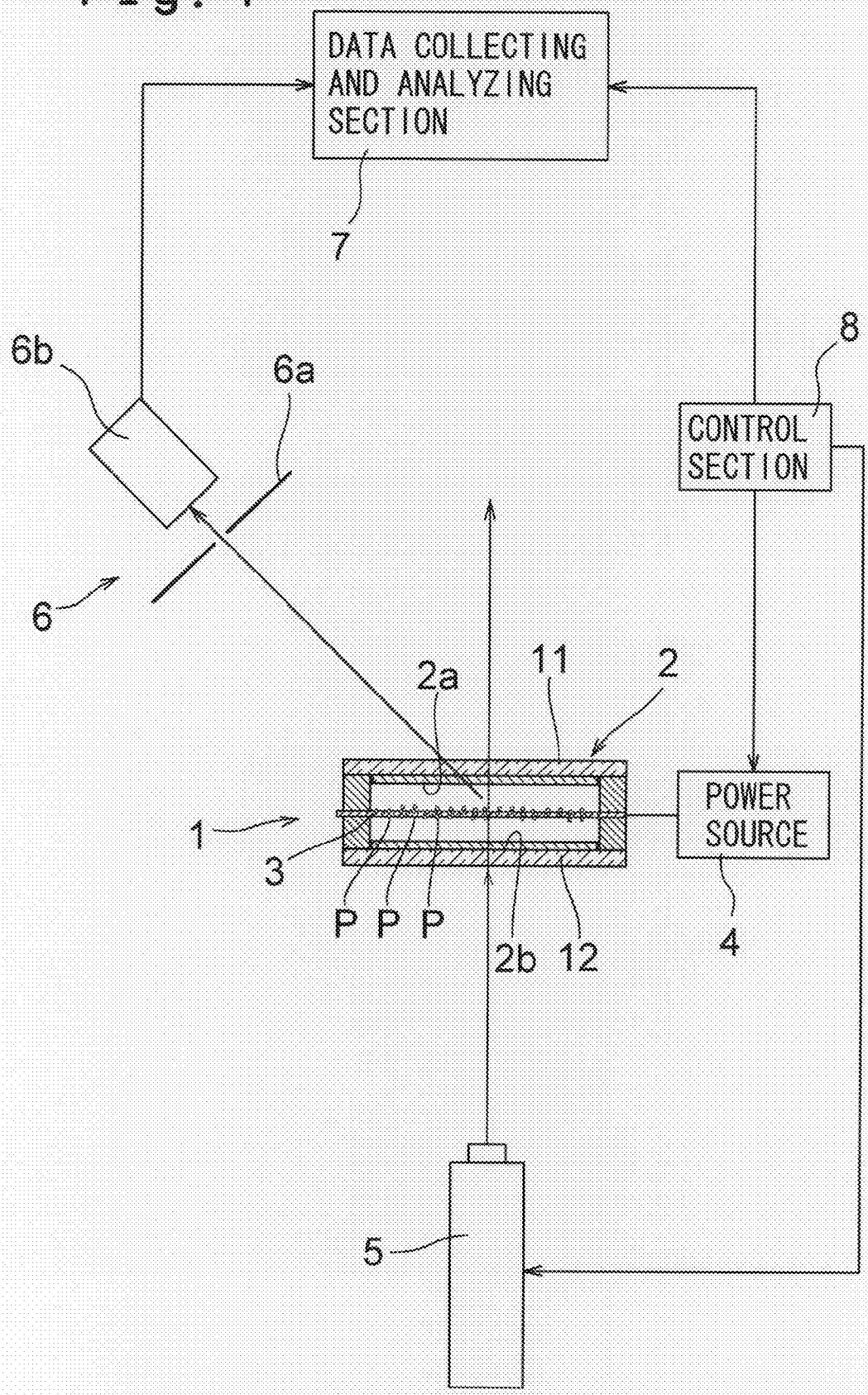
FIG. 1 shows an overall configuration according to an embodiment of the present invention, including a schematic diagram showing an optical configuration and a block diagram showing an electrical configuration.

1 Cell
2a, 2b Electrodes
3 Dielectric sheet
3a Slit
3b Through hole
4 Power source
5 Irradiation optical system
6 Detection optical system
6a Pinhole 6b Light detector
7 Data collecting and analyzing section
8 Control section

BEST MODE FOR CARRYING OUT THE INVENTION

Embodiments of the present invention will hereinafter be described with reference to the accompanying drawings.

FIG. 1 shows an overall configuration according to an embodiment of the present invention, including a schematic diagram showing an optical configuration and a block diagram showing an electrical configuration.

The apparatus includes mainly: a cell 1 for storing a sample having particles dispersed movably in a medium, for example, a sample having particles dispersed in a liquid, or a sample composed of a gel having particles dispersed movably therein; a pair of electrodes 2a and 2b provided in the cell 1; a dielectric sheet 3 also provided in the cell 1; a power source 4 for applying a voltage between the pair of electrodes 2a and 2b; an irradiation optical system 5 for applying a parallel light flux to the cell 1; a detection optical system 6 for detecting diffracted light from a diffraction grating generated by the dielectric sheet 3; a data processing and analyzing section 7 for collecting outputs from the detection optical system 6 to perform various analyses; and a control section 8 for controlling the entire measurement process.

As shown in the schematic cross-sectional view of FIG. 2 (A) or 2 (B), the cell 1 includes two mutually parallel wall bodies 11 and 12 made of transparent material such as glass, and the flat plate-like electrodes 2a and 2b are formed on the inner surface of the respective wall bodies 11 and 12. In the present embodiment, the pair of electrodes 2a and 2b are transparent ones such as ITO.

Figure 3A:
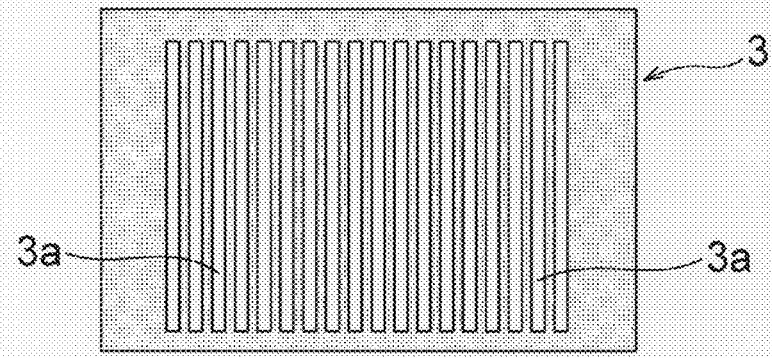
FIG. 3 illustrates the structure of a dielectric sheet in FIG. 1, where (A) is a front view and (B) is a transverse sectional view.
Figure 3B:
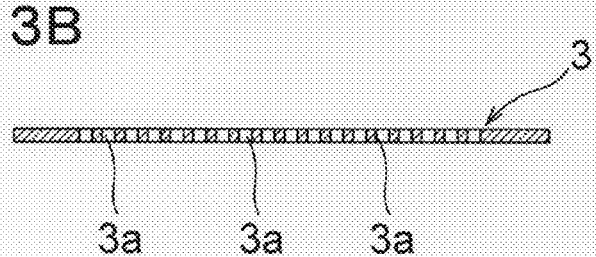

As shown in FIG. 3, the dielectric sheet 3, which is made of, for example, fluororesin to have a high chemical resistance and a high visible light permeability, includes multiple slits 3a bored in parallel with each other. The thickness is preferably several micrometers or more for easy handling. The width and pitch of the slits 3a are within a range from 1 to 10 μm and may be fabricated through, for example, laser processing or photolithographic techniques. The thus arranged slits 3a form a diffraction grating. It is noted that if the medium (medium liquid) is water, the chemical resistance is not particularly needed and an easily workable material may be selected appropriately.

The dielectric sheet 3 is arranged at the intermediate position between and in parallel with the transparent wall bodies 11 and 12, and is fixed with being surrounded and sandwiched by spacers or the likes that exist between the wall bodies 11 and 12.

The irradiation optical system 5 outputs substantially monochromatic light with being shaped into a substantially parallel light flux, and the output light is applied into the cell 1 through the one transparent wall body 12 of the cell 1 and the transparent electrode 2b. As a light source of the irradiation optical system 5, an element that emits only monochromatic light such as a laser or an LED is easy to use. However, a continuous wavelength light source may also be used if the light thereof is made quasi-monochromic through a band pass filter, a spectrometer, or the like. A spectrum bandwidth of the light may be about several tens nm or less, for example, in the visible wavelength range. The irradiation light from the irradiation optical system 5 is applied to the diffraction grating formed by the slits 3a of the dielectric sheet 3 in the cell 1 through the one transparent wall body 12 and the transparent electrode 2b, and the light transmitting through the diffraction grating travels out of the cell 1 through the other transparent electrode 2a and transparent wall body 11. The light from the irradiation optical system 5 is diffracted by the diffraction grating formed by the slits 3a of the dielectric sheet 3 in the cell 1.

The detection optical system 6 is arranged in a position where to detect the diffracted light of a certain order. The detection optical system 8 includes, for example, a pinhole 6a and a light detector 6b. The detection optical system 6 measures the temporal change in the intensity of diffracted light from the slits 3a of the dielectric sheet 3 in the cell 1.

Now, between the pair of electrodes 2a and 2b is applied an AC voltage from the power source 4. This voltage application causes an electric field to occur in the cell 1. As shown in the principle diagram of FIG. 4, the electric lines of force 2c are concentrated and thickened in the vicinity of the slits 3a of the dielectric sheet 3 to be a high-gradient electric field there. When such a spatially periodic electric field occurs in the cell 1, particles P to be measured move dielectrophoretically. If a positive dielectrophoretic force acts on the particles P, the particles P move dielectrophoretically toward the areas where the electric lines of force 2c are concentrated, that is, toward the slits 3a.

Figure 5:
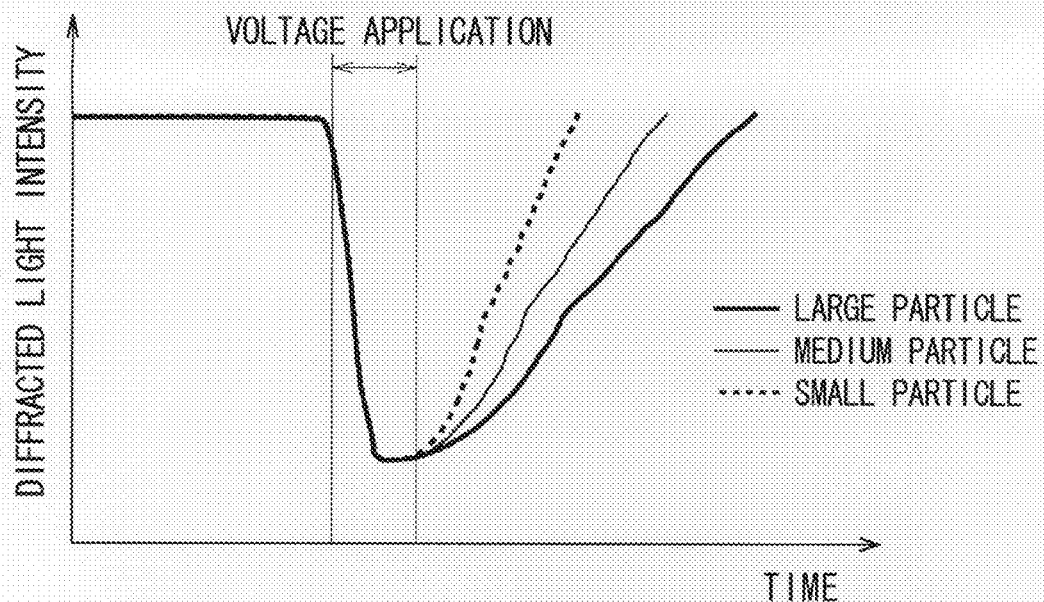
FIG. 5 is a graph showing an example of measurement results according to the embodiment of the present invention.

The particles P in the cell 1 are dispersed homogeneously in the medium as shown in FIG. 5 (A) when no such an electric field is applied to, while concentrated in such a manner as to cover the slits 3a of the dielectric sheet 3 as shown in FIG. 5 (B) when such a spatially periodic electric field is applied to. This concentration of the particles P around the slits 3a reduces the contrast of the diffraction grating formed by the slits 3a of the dielectric sheet 3 relative to the state shown in FIG. 5 (A) where the particles P are dispersed homogeneously.

Figure 4:
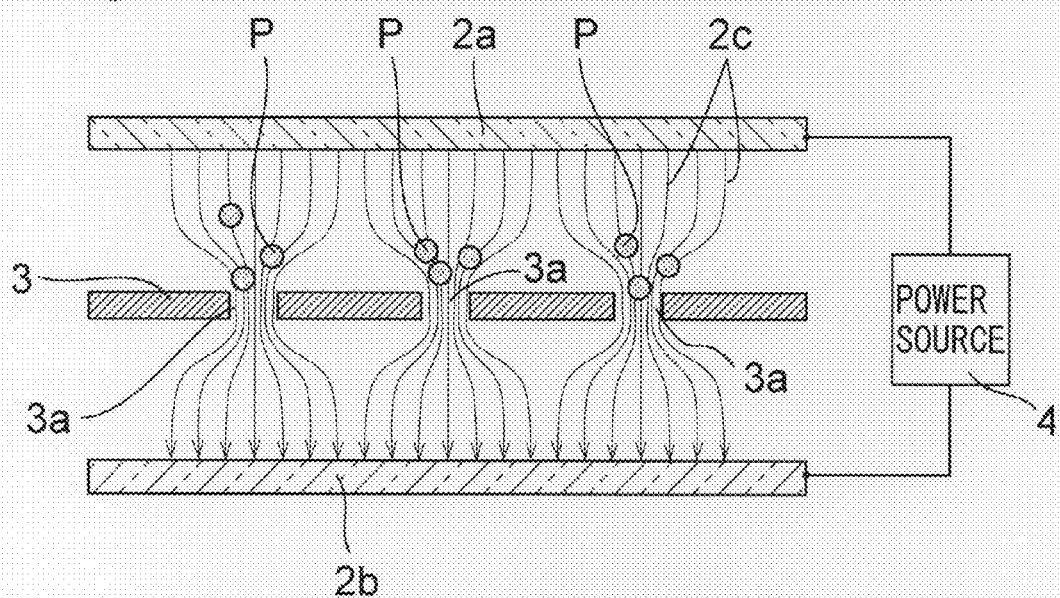
FIG. 4 illustrates the principle of the embodiment of the present invention.

Accordingly, the intensity of diffracted light generated by the parallel light flux passing through the slits 3a is reduced when in the state shown in FIG. 5 (B) relative to the state shown in FIG. 5 (A). After the application of the voltage between the electrodes 2a and 2b, when the application of the voltage is stopped, the particles P diffuse freely to recover such a homogeneously-dispersed state as shown in FIG. 4 (A) and thus the diffraction grating recovers its original high contrast. The diffusion rate of the particles P after stopping the application of the voltage depends on the diffusion coefficient and therefore the size of the particles P. Therefore, as exemplified in the graph of FIG. 6, information about the diffusion coefficient and therefore the size of the particles P can be obtained from data after stopping the application of the voltage among diffracted light intensity detection data.

Performing the above-described measurement for multiple kinds of sample particles under the same condition allows information about the magnitude relation of the diffusion coefficient and therefore the particle size between the sample particles to be obtained. Also, performing a calibration preliminarily using several kinds of reference particles having their respective known diffusion coefficients and therefore particle sizes allows quantitative information about the diffusion coefficient and therefore the size of the sample particles to be obtained. According to this approach, the data collecting and analyzing section 7 calculates the diffusion coefficient and/or size of the particles P.

What is particularly remarkable in the above-described embodiment is that the contrast of the diffraction grating formed by the slits of the dielectric sheet varies due to the migration of the sample particles, and the variation is taken as a change in the intensity of diffracted light to calculate the diffusion coefficient or size of the particles. This approach allows the diffusion coefficient and therefore the size of the particles to be measured under higher S/N relative to conventional methods of measuring the fluctuation of scattered light from each particle, such as the dynamic scattering method. At the same time, this approach can prevent absorption of particles onto the electrodes and/or the surfaces where the electrodes are formed and also the occurrence of an electrode reaction, unlike methods of measuring the intensity of diffracted light from a diffraction grating generated from the density distribution of particles using a regularly arranged electrode pair.

The above embodiment describes the behavior of particles on which a positive dielectrophoretic force acts. As for particles on which a negative dielectrophoretic force acts, the application of an AC voltage between the electrodes 2a and 2b causes the particles to migrate away from the slits 3a, resulting in an increase in the contrast of the diffraction grating formed by the slits 3a and therefore in the intensity of diffracted light from the diffraction grating relative to the state where the particles are dispersed homogeneously. In this state, when the application of the voltage is stopped, the particles diffuse freely to recover their original dispersion state and thus the diffraction grating recovers its original contrast, and whereby the intensity of the diffracted light decreases after stopping the application of the voltage, contrary to the description above. The diffusion coefficient and therefore the size of the particles can be calculated from the rate of the decrease in the intensity of the diffracted light in the same manner as above.

Although the above description exemplifies the case where the particles migrate dielectrophoretically with the application of an AC voltage and therefore the formation of an AC electric field within the sample in the cell 1, the particles may migrate electrophoretically with the application of a DC voltage within the sample in the cell 1 and then the application of the DC voltage may be stopped to cause the particles to diffuse freely so that the diffusion coefficient and the particle size can be calculated using the diffracted light intensity during the diffusion process.

Figure 6A:
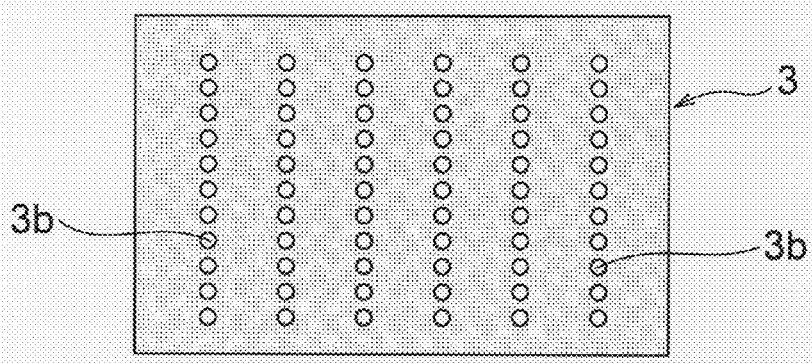
FIG. 6 is an illustrative view showing another structural example of the dielectric sheet according to the present invention, where (A) is a front view and (B) is a transverse sectional view.
Figure 6B:
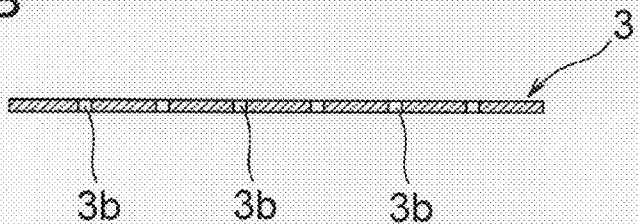

Although the above embodiment exemplifies the case where multiple mutually parallel slits are bored in the dielectric sheet to form a diffraction grating, multiple mutually parallel arrays of through holes 3b may be formed in the dielectric sheet 3 to form a diffraction grating as shown in FIG. 6, which can exhibit the same advantage as the above-described embodiment.

Figure 7A:
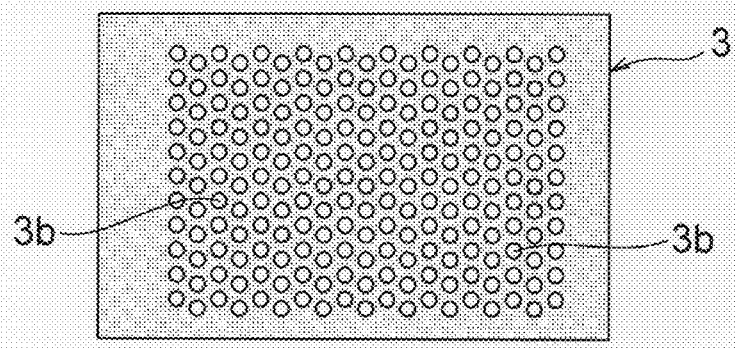
FIG. 7 is an illustrative view showing still another structural example of the dielectric sheet according to the present invention, where (A) is a front view and (B) is a transverse sectional view.
Figure 7B:
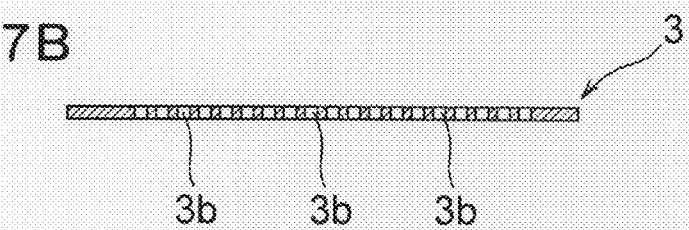
Figure 8:
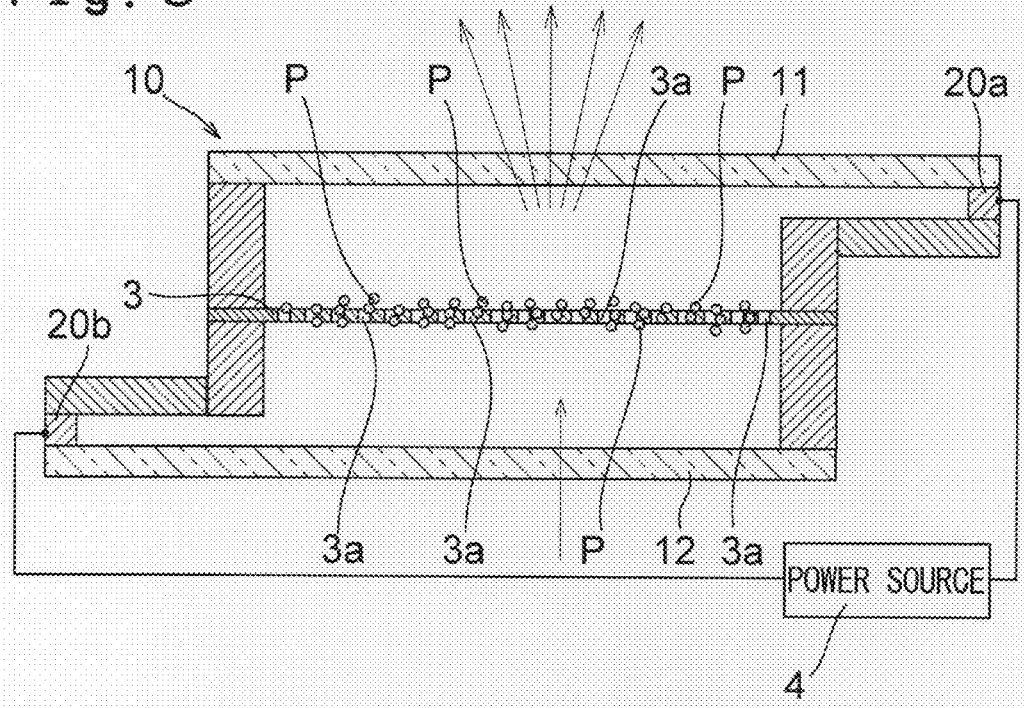
FIG. 8 is a schematic cross-sectional view showing another structural example of the cell and electrodes according to the present invention.

Further, the multiple through holes 3b may not be formed in such a one-dimensionally aligned manner as shown in FIG. 6, but in their entirety may form hole arrays in mutually different directions such as vertical, horizontal, and oblique directions as shown in FIG. 7. In this case, diffracted light is generated according to the direction of each hole array, and the detection optical system is only required to detect the intensity of any diffracted light.

The cell 1 and the electrodes 2a and 2b are also not restricted to the arrangement described in the above embodiment. As shown in FIG. 7, it may be arranged, for example, that a pair of opaque electrodes 20a and 20b are provided at an end portion of the respective transparent wall bodies 11 and 12 of the cell 1 and a line connecting the electrodes 20a and 20b runs obliquely across the dielectric sheet 3 that is arranged between and in parallel with the wall bodies 11 and 12, and that irradiation light from the irradiation optical system 5 enters the cell 1 directly through the one wall body 12 and diffracted light from a diffraction grating formed by the slits 3a or arrays of through holes 3b in the dielectric sheet 3 travels out of the cell through the other wall body 11.

Industrial Applicability

In accordance with the present invention, the diffusion coefficient and/or size of nanoparticles can be measured under high S/N, and particles cannot be absorbed around the electrodes through the measurement, so that the electrodes are less likely to be damaged and electrode reactions are also less likely to occur. In addition, since the dielectric sheet is inexpensive, it may be disposable with an easily detachable arrangement. Furthermore, unlike the technique described in Patent Document 1 in which a voltage is applied to a periodic electrode pair to generate a diffraction grating of particles, there can occur no trouble in that diffracted light through the electrode pair may be a noise component.

The invention claimed is:

1. An apparatus for measuring nanoparticles comprising: a cell for storing therein a sample having particles dispersed movably in a medium; a power source for generating an AC or DC voltage; a pair of electrodes formed inside the cell in such a manner as to approximately face each other and to which a voltage is applied from the power source; a dielectric sheet arranged between the pair of electrodes and adapted to form a spatially periodic electric field in the cell with the application of the voltage between the electrodes; an irradiation optical system for applying a parallel light flux into the cell; a detection optical system for detecting diffracted light generated by the parallel light flux transmitting through the cell; control means for controlling the application of the voltage from the power source to the pair of electrodes; and data processing means for calculating the diffusion coefficient and/or size of the particles in the cell from the temporal change of the diffracted light through the application of the voltage and the stopping or modulation of the application.

2. The apparatus for measuring nanoparticles according to claim 1, wherein the cell comprises wall bodies made of transparent material and facing each other, the pair of electrodes are transparent ones and formed on the mutually facing wall bodies, the dielectric sheet is provided between and in parallel with the wall bodies, the irradiation optical system is adapted to apply a parallel light flux into the cell through one of the transparent electrodes, and the detection optical system is adapted to detect diffracted light through the other transparent electrode.

3. The apparatus for measuring nanoparticles according to claim 1, wherein the cell comprises wall bodies made of transparent material and facing each other, the pair of electrodes are each formed at an end portion of each wall body, the dielectric sheet is provided between and in parallel with the wall bodies, the irradiation optical system is adapted to apply a parallel light flux into the cell not through either of the pair of electrodes but through one of the wall bodies, and the detection optical system is adapted to detect diffracted light not through either of the pair of electrodes but through the other wall body.

4. The apparatus for measuring nanoparticles according to claim 1, wherein the dielectric sheet is formed to include a plurality of mutually parallel slits.

5. The apparatus for measuring nanoparticles according to claim 1, wherein the dielectric sheet is formed to include a plurality of mutually parallel hole arrays, each of the hole arrays including a plurality of through holes formed in a one-dimensional direction.

6. The apparatus for measuring nanoparticles according to claim 1, wherein the dielectric sheet is formed to include a plurality of through holes, each of the through holes being formed in a positional relationship of forming arrays in a plurality of directions.

7. The apparatus for measuring nanoparticles according to claim 2, wherein the dielectric sheet is formed to include a plurality of mutually parallel slits.

8. The apparatus for measuring nanoparticles according to claim 3, wherein the dielectric sheet is formed to include a plurality of mutually parallel slits.

9. The apparatus for measuring nanoparticles according to claim 2, wherein the dielectric sheet is formed to include a plurality of mutually parallel hole arrays, each of the hole arrays including a plurality of through holes formed in a one-dimensional direction.

10. The apparatus for measuring nanoparticles according to claim 3, wherein the dielectric sheet is formed to include a plurality of mutually parallel hole arrays, each of the hole arrays including a plurality of through holes formed in a one-dimensional direction.

11. The apparatus for measuring nanoparticles according to claim 2, wherein the dielectric sheet is formed to include a plurality of through holes, each of the through holes being formed in a positional relationship of forming arrays in a plurality of directions.

12. The apparatus for measuring nanoparticles according to claim 3, wherein the dielectric sheet is formed to include a plurality of through holes, each of the through holes being formed in a positional relationship of forming arrays in a plurality of directions.

* * * * *